United States Patent [19]

Chiaramonte

[11] 4,108,642

[45] Aug. 22, 1978

[54] ALLOY FOR PREPARING DENTURES THEREFROM

[75] Inventor: Vincent T. Chiaramonte, Baldwin, N.Y.

[73] Assignee: Apex Dental Lab. Inc., New York, N.Y.

[21] Appl. No.: 795,954

[22] Filed: May 11, 1977

[51] Int. Cl.² .................. C22C 30/00; C22C 19/05
[52] U.S. Cl. .................... 75/134 F; 75/171
[58] Field of Search ............. 75/134 F, 134 N, 171

[56] References Cited

U.S. PATENT DOCUMENTS

| 2,506,526 | 5/1950 | Tifft | 75/171 |
|---|---|---|---|
| 2,636,818 | 4/1953 | Low | 75/171 |
| 2,827,373 | 3/1958 | Prasse | 75/134 |
| 3,121,629 | 2/1964 | Mann | 75/171 |
| 3,148,053 | 9/1964 | Spaletta | 75/134 |
| 3,464,817 | 9/1969 | Griffiths | 75/171 |

FOREIGN PATENT DOCUMENTS

| 4,632,846 | 8/1967 | Japan | 75/134 F |
|---|---|---|---|
| 277,271 | 4/1962 | Netherlands | 75/172 G |
| 286,927 | 3/1953 | Switzerland | 75/134 F |
| 286,926 | 3/1953 | Switzerland | 75/134 F |

OTHER PUBLICATIONS

Sims et al, "The Superalloys," Wiley, N.Y., 1972, p. 579.

Primary Examiner—L. Dewayne Rutledge
Assistant Examiner—Upendra Roy
Attorney, Agent, or Firm—James P. Malone

[57] ABSTRACT

An alloy for dentures with procelain caps which forms a good bond comprising 15 to 30% chromium, 30 to 60% nickel, 15 to 30% cobalt, 1 to 5% iron, and 1 to 2% beryllium. Another dental alloy comprises by weight about 22.2% Cr, 9.7% Co, 29.4% Ni, 29.4% Fe, 4.85% Al and 4.85% Mo.

3 Claims, No Drawings

ALLOY FOR PREPARING DENTURES THEREFROM

This invention relates generally to metal alloys. More particularly the present invention relates to alloys suitable for dental castings and copings and methods of melting such alloys and forming the dental castings.

Dental copings, as is well known, are used as jackets or caps for prepared metal denture bases, and are designed to carry a porcelain or plastic coated metal crown, jacket or cap. It is this metal to procelain contact area that must form a bond. This bond however, is often the cause of failure of the tooth restoration due to the lack of adequate adhesion between the porcelain and the metal.

This invention has as one of its prime objectives the provision of an alloy of superior strength, adhesion to porcelain and plastic and to the prepared tooth stub, and of low cost.

Variations in temperature of the mouth due to intake of hot and cold liquids and foods must not cause a separation of the tooth-metal alloy or metal alloy-porcelain connections. Hence, a further primary object is the provision of an alloy with a coefficient of expansion substantially the same as that of the tooth stub or residue, and as that of the porcelain and of the cemented connection to the tooth and the porcelain.

Another object of the invention is to make available an alloy material strongly adherent to and non-separable from porcelain or plastic and which is resistant (1) to the range of acidity and basicity to which the mouth may be subjected, (2) to erosion and wear during a lifetime of grinding, (3) to embrittlement and cracking from biting pressures to which teeth normally are subjected, (4) to tarnishing and corrosion by food elements and in general the oral environment.

A still further object of the invention is the provision of an alloy having a melting point or fusion point higher than that of the porcelain to be applied to it as a jacket or cap, but not too high for the usual dental investment materials, and the further provision of an alloy of ready castability which offers a choice of silver, gold-yellow, or a white color, i.e., with porcelain jacket or cap.

A further object of the invention is to provide a process for making such a dental alloy, and to provide it in a form that is most expeditiously handled in the preparation of the dentures.

Still further objects and advantages will be evident from the more detailed description of the alloy and the process of making it.

Various uses for the alloy will become apparent from the description which follow, and while examples are given with references to the dental applications, it is not to be considered as limiting the invention thereto. Many of the properties of the alloy, for instance, are prerequisites for other uses, e.g., jewelry, watches and the like.

The dentures to which the present invention relates are made by casting the metals or alloys in refractories. In accomplishing the objects of this invention the coping alloy is manufactured by appropriately combining in selected proportions, major amounts of nickel, cobalt and chromium with smaller amounts of gold and iron. Minor amounts of palladium and beryllium, and/or silicon are included to modify certain properties of the alloy for specific dental applications, i.e., crown and bridge restorations, fillings, inlays, etc.

The prior art has shown the dental use of alloys prepared from (1) chromium, cobalt, nickel, iron, tungsten and carbon (Prage, U.S. Pat. No. Re. 20,877), (2) chromium, nickel, cobalt, platinum and minor amounts of beryllium, silicon and molybdenum (Mann, U.S. Pat. No. 3,121,629, (3) nickel, cobalt, chromium and gold (Tifft, U.S. Pat. No. 2,506,526, (4) a combination of chromium, nickel, cobalt, iron, with minor amounts of manganese, boron and silicon (Szabo, U.S. Pat. No. 2,182,041). None of these compositions of the prior art fulfills all of the desired objectives of the present invention, either failing in adhesive properties to the porcelain material, in brittleness, in coeficients of expansion, or in desired melting point or color.

It has been found that the proportions of the elements included in the composition forming the alloy are important in order to attain the desired balance of properties for wide dental usage, exceptional wear and hardness, being burnished; proper coefficient of expansion for porcelain and tooth materials; high strength and not brittle; higher melting point than porcelain to permit complete wetting to the molten porcelain and ultimately a strong adhesion between the alloy and porcelain; low-cost to permit wide usage for individuals of the lower income spectrum.

The Examples set forth the range of compositions of the alloy of the present invention. The chromium and cobalt can be varied slightly to adjust hardness and the burnishing factor; the nickel toughens and softens the Cr-Co mix; the beryllium, it is believed, serves as a deoxidizing agent. Palladium can be omitted where slightly increased oxides are desired on the surface of the denture for slightly increased adhesion; or when a "whiter" color is wanted, or when a higher melting point is desired. The iron is added to improve ductility and bonding of the alloy without sacrifice of hardness.

| COMPOSITION OF NEW ALLOY | | | |
|---|---|---|---|
| Example A: Metal | Broad Percent | Percent Preferred | Percent Weight Alternate |
| Chromium | 15 to 30% | 20 to 25% | 21.94 |
| Nickel | 30 to 60% | 40 to 55% | 50.01 |
| Cobalt | 15 to 30% | 20 to 30% | 25.00 |
| Iron | 1. to 5.% | 1. to 3.% | 1.36 |
| Beryllium | 1. to 2.% | 1.5 to 1.8% | 1.69 |
| Example B: | | | |
| Chromium | 15 to 30% | 20 to 25% | |
| Nickel | 30 to 60% | 40 to 50% | |
| Cobalt | 15 to 30% | 20 to 25% | |
| Palladium | 0 to 40% | 3. to 15% | |
| Gold | 0 to 40% | 3. to 15% | |

Palladium or Gold may be used separately or together.

It is possible to provide the compositions of Examples A & B each with a gold color capability in addition to a silver appearance.

Gold color is achieved by adding 1 to 40% gold which gives gold color in accordance with the amount of gold added.

| Example C: | |
|---|---|
| Chromium | 2 pennyweights, 7 grains |
| Cobalt | 1 pennyweight, 0 grains |
| Nickel | 3 pennyweights, 2 grains |
| Iron | 3 pennyweights, 0 grains |
| Aluminum | 0 pennyweights, 12 grains |
| Molybdenum | 0 pennyweights, 12 grains |

This converts to 22.2% chromium, 9.7% cobalt, 29.4% nickel, 29.4% iron, 4.85% aluminum, 4.85% molybdenum, by weight.

The gold component has the effect of lowering the melting point and also improves mechanical properties. The melting point of the preferred composition of Example A with 4.7% Gold is about 2,250° F. whereas without the gold, the alloy from the remaining metals as shown melts at about 2,400° F.

These alloy compositions have been found to provide dental copings of high strength, accuracy in casting, low cost, good adhesion to porcelain, as well as having the capability of accepting polishing to a high luster.

The development of a surface oxide in the treatment of the casting during the firing cycle of the opaque on the metal provides the proper bonding conditions at the interface. These surface oxides are developed by careful control of the pretreatment temperature in a vacuum. The treatment is exemplified in a typical example described hereinafter.

In the manufacture of dentures; the alloy when fully molten is centrifugally cast into a mold where rapid solidification occurs. The present invention utilizes the usual steps except that the heating of the casting rings is carried to 1500° F. and the centrifuge preferably has a more powerful spring. The investments are of the high heat type and the heat-soaking period is approximately thirty minutes.

An important consideration for the casting is its ability to adhere to lower-temperature fusing porcelains. The present alloy forms an actual bond, which is believed to be a chemical bond, with the procelain when the casting surface is carefully prepared at an appropriate temperature and with the use of the high vacuum, as long as the porcelains used have the proper coefficient of expansion.

In each example a conventional centrifugally molded casting was used. The casting of single units or of soldered multiple dental units were smoothed with a sand-blaster, using aluminous oxide as sand, then trimmed and ground to the desired thickness, cleaned in alcohol ultrasonically for about 5 minutes, then dried. Conventional opaque coating was applied to the castings, one very thin, then fired. The second coating was applied thick, then fired. After the preceding steps the gingeval and incisal porcelain are applied, then fired in the conventional manner.

A vacuum oven was preheated to about 600° F. and the casting with a porcelain cap loosely mounted was inserted therein. A vacuum of thirty inches was rapidly and immediately applied to the oven to remove the air therefrom and the temperature was raised rapidly to 1950° F. to form a metal oxide on the metal surface. A small amount of air is always present and it is enough to give oxide. The oven was then cooled to 600° F. and the casting was removed therefrom. It was observed to have a light golden color and the bonds of the metal to porcelain were excellent. They did not crack or tarnish under normal usage when installed in the mouths of patients.

EXAMPLE D

In the finished product, after the porcelain has been applied, the exposed metal is polished and cleaned ultrasonically in alcohol and preheated in the furnace to 1,000°. The unit is inserted in the oven and allowed to heat uniformly for 2 minutes (minimum) gradually increasing the temperature with no vacuum applied, it is constantly observed and between 1,000° and 1,250° a gold color at all the exposed metal (2 to 6 minutes) will take place. If it is left in the oven more than 6 minutes, it will turn black so it is removed from the oven and allowed to cool while it has the desired gold color.

The finished restoration will appear to be just like gold (color).

EXAMPLE E

Example D was repeated. Following the final polishing the dentures were returned to a 1000° F oven and heat soaked at 1000° to 1200° F. until a golden color again developed. This color development may be due to diffusion or migration of the gold to the surface of the casting during heat soaking.

EXAMPLE F

The process was repeated except that the alloy contained no beryllium, and consisted of 21.8% chromium, 46.5% nickel, 24.2% cobalt, 4.8% gold, 0.5% iron and 2.2% palladium. The heat casting required a temperature of 2000° F instead of 1950° F to to develop the same properties as obtained previously. The casting was good for porcelain facing and not for full coverage, excellent for plastic and easy to finish, polish and solder.

EXAMPLE G

The process was repeated but both beryllium and palladium were omitted from the alloy. The vacuum and temperatures of oven treatment were the same. An excellently bonded denture was obtained from the alloy comprising chromium (22.4%), nickel (47.5%), cobalt (24.8%), gold (4.7%) and iron (0.55%).

EXAMPLE H

Example G was repeated except that 0.45 part of silicon was added in place of 0.45 parts of the nickel, i.e., 47.0 parts nickel was employed instead of 47.5% nickel. Color and other physical properties including adhesive strength were excellent.

EXAMPLE I

Example G was repeated except that the iron content was omitted. The resulting alloy was strong and showed good adhesion, but was brittle and not sufficiently ductile for most dental applications.

EXAMPLE J

An alloy consisting of 21.9% chromium, 47.1% nickel, 24.2% cobalt, 4.8% gold, 0.55% iron and 1.45% beryllium was centrifugally molded and was thereafter treated as previously, the procelain being more difficult to bond with the alloy. The final denture had an excellent gold color, a strong alloy-porcelain bond, and was hard but not brittle.

From these examples it is apparent that my alloys has excellent adhesion to porcelain and other excellent, physical properties and offers numerous advantages to the dental industry. Also, the alloy has properties that make it quite useful to other industrial applications, e.g., jewelry, watch bearings, and the like, Hence it is not intended that the utility of the alloy be limited to the examplified dental applications.

Other variations may be possible without departing from the practice of my invention, e.g., the heat treatment of my alloy casting may be conducted in an oven at atmospheric pressure provided that the oven be maintained substantially free of oxygen and air by use of an inert gas such as helium, argon, neon, etc. The role of the vacuum in limiting the amount of oxidation also is accomplished by replacing the air with an inert gas. Thus, the examples given herein should not be construed as limiting but rather illustrative of my invention. The inherent strength, resilience, hardness, rigidity, non-tarnishing and wearing characteristics together with good melting range and properties of adhesion of my alloy, make it possible to produce thin films, slender parts and castings for the dental profession. My preferred form of the alloy and my method of carrying out the casting procedure preferably by melting and casting the alloy in the usual centrifuging and molding equipment, and development of an effective bond to porcelain materials, enhances the value of my invention for present day dental procedures. However, the use of the alloy and its inherent good properties is not dependent on specific techniques. Rather it is amenable and adaptable for use by modified techniques.

As dental technology advances I anticipate that my alloy can readily adapt to serve for manufacture of dental copings far into the future. Thus, I have replaced present costly gold and noble metals in the dental field by an economic alloy offering services to the low-income group which today can ill-afford the costly dentures.

It has been found that the inclusion of Be in the composition A produces not only the deoxydizing effect in the casting which is well known but more importantly it enables the metal composition to have a coefficient of thermal expansion slightly higher than that of the porcelain. Porcelain, being strongest when under some tension, adds to the bond strength. The purpose of this is to prevent the cracking of the porcelain veneer on the metal due to changes in temperature. With respect to Example A, the incorporation of iron is necessary because the iron is oxidized and it is this iron oxide which can be bound to the porcelain in a chemical way. The chromium, nickel and cobalt would not under these conditions, appear to form an oxide and therefore there would be no adherence between the metal and the porcelain were it not for the presence of iron and its iron oxide.

The vacuum of 30 inches is used principally in order to evacuate the air and to standardzie the procedure so as to control the oxidation that is occurring. At a minimum oxidation environment, the oxidation can be controlled more readily on a time basis. The vacuum that is mentioned can be varied from approximately 28 inches of mercury to 30 inches of mercury. The temperature is increased rapidly from about 30° per minute to 80° or perhaps 100° per minute. If less speed were used in raising the temperature, some porcelains would not be useful.

I claim:
1. The alloy comprising:
15 to 30% chromium,
30 to 60% nickel,
15 to 30% cobalt,
1 to 5% iron, and
1 to 2% beryllium.
2. The alloy comprising:
20 to 25% chromium,
40 to 55% nickel,
20 to 30% cobalt,
1 to 3% iron, and
1.5 to 1.8% berylllium.
3. The alloy in percent weight comprising about:
22.2% chromium,
9.7% cobalt,
29.4% nickel,
29.4% iron,
4.85% aluminum,
4.85% molybdenum.

* * * * *